United States Patent
McGinley

(10) Patent No.: US 11,000,292 B2
(45) Date of Patent: May 11, 2021

(54) MEASUREMENT SYSTEM FOR USE WITH SURGICAL BURR INSTRUMENT

(71) Applicant: McGinley Engineered Solutions, LLC, Casper, WY (US)

(72) Inventor: Joseph C. McGinley, Casper, WY (US)

(73) Assignee: McGinley Engineered Solutions, LLC, Casper, WY (US)

( * ) Notice: Subject to any disclaimer, the term of this patent is extended or adjusted under 35 U.S.C. 154(b) by 109 days.

(21) Appl. No.: 16/401,400

(22) Filed: May 2, 2019

(65) Prior Publication Data
US 2019/0254685 A1 Aug. 22, 2019

Related U.S. Application Data

(62) Division of application No. 15/330,825, filed on Nov. 7, 2016, now Pat. No. 10,321,920.
(Continued)

(51) Int. Cl.
*A61B 17/16* (2006.01)
*A61B 17/32* (2006.01)
(Continued)

(52) U.S. Cl.
CPC ...... *A61B 17/1626* (2013.01); *A61B 17/1633* (2013.01); *A61B 17/1695* (2013.01);
(Continued)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 1,831,813 A * 11/1931 Levedahl ................ B23B 49/02
408/81
2,883,891 A * 4/1959 Robinson ................ B25F 5/003
408/112
(Continued)

FOREIGN PATENT DOCUMENTS

DE 102011056927 6/2017
WO 9724991 7/1997
(Continued)

*Primary Examiner* — Eric S Gibson
(74) *Attorney, Agent, or Firm* — Holzer Patel Drennan

(57) ABSTRACT

Use of measurement system and detection module with a burr instrument for surgical procedures. The measurement system may include sensors (e.g., displacement, acceleration, and/or force sensors) that may be utilized to detect potentially hazardous operation of the burr instrument. For example, when penetrating through the cortex of the bone the measurement system may be operated in a unicortical mode such that when the burr passes through the cortex of the bone, the instrument operating may be arrested to avoid damage to surrounding tissue. Moreover, the system may be utilized to detect a slip or sudden loss of contact of the burr instrument such that the instrument may be arrested to avoid damage to surrounding tissue. Furthermore, the burr instrument may have a predetermined ramp-up speed.

8 Claims, 6 Drawing Sheets

Related U.S. Application Data

(60) Provisional application No. 62/252,193, filed on Nov. 6, 2015.

(51) Int. Cl.
*A61B 90/00* (2016.01)
*A61B 17/00* (2006.01)

(52) U.S. Cl.
CPC .... *A61B 17/32002* (2013.01); *A61B 17/1628* (2013.01); *A61B 2017/00022* (2013.01); *A61B 2017/00075* (2013.01); *A61B 2090/062* (2016.02); *A61B 2090/065* (2016.02); *A61B 2090/08021* (2016.02)

(58) Field of Classification Search
CPC ............ A61B 17/1622; A61B 17/1624; A61B 17/1626; A61B 17/1628
See application file for complete search history.

(56) References Cited

U.S. PATENT DOCUMENTS

| | | | |
|---|---|---|---|
| 3,804,544 A | 4/1974 | Adams | |
| 4,014,621 A | 3/1977 | Johnson et al. | |
| 4,063,356 A | 12/1977 | Hepworth | |
| 4,157,231 A * | 6/1979 | Phillips | E21B 19/086 408/1 R |
| 4,310,269 A * | 1/1982 | Neu | B23B 47/32 408/10 |
| 4,329,092 A * | 5/1982 | Ponitzsch | B23B 45/04 408/10 |
| 4,329,095 A * | 5/1982 | Schmuck | B23B 49/006 408/112 |
| 4,644,335 A * | 2/1987 | Wen | G01H 1/003 340/680 |
| 4,710,075 A | 12/1987 | Davison | |
| 4,723,911 A | 2/1988 | Kurtz | |
| 4,765,333 A | 8/1988 | Bray | |
| 4,867,158 A | 9/1989 | Sugg | |
| 4,951,690 A | 8/1990 | Baker | |
| 5,013,194 A | 5/1991 | Wienhold | |
| 5,014,793 A * | 5/1991 | Germanton | B25B 21/00 173/181 |
| 5,022,798 A | 6/1991 | Eckman | |
| 5,071,293 A * | 12/1991 | Wells | B23Q 5/263 408/112 |
| 5,133,728 A | 7/1992 | Petersen | |
| 5,139,376 A | 8/1992 | Pumphrey | |
| 5,161,921 A | 11/1992 | Corsi | |
| 5,277,799 A | 1/1994 | Bransch | |
| 5,361,504 A | 11/1994 | Huang | |
| 5,380,333 A | 1/1995 | Meloul et al. | |
| 5,411,503 A * | 5/1995 | Hollstien | A61B 17/1707 606/80 |
| 5,533,842 A * | 7/1996 | Johnson | B23Q 5/265 408/130 |
| 5,538,423 A * | 7/1996 | Coss | A61C 1/0015 408/8 |
| 5,584,838 A * | 12/1996 | Rona | A61B 17/1707 324/226 |
| 5,599,142 A * | 2/1997 | Fujimoto | B23Q 15/12 408/10 |
| 5,613,810 A * | 3/1997 | Bureller | B23Q 15/12 408/11 |
| 5,810,828 A * | 9/1998 | Lightman | A61B 17/164 606/80 |
| 5,902,306 A | 5/1999 | Norman | |
| 5,961,257 A * | 10/1999 | Bettini | E01B 31/24 408/97 |
| 5,980,248 A * | 11/1999 | Kusakabe | A61C 1/0007 433/131 |
| 6,033,409 A * | 3/2000 | Allotta | A61B 17/1622 606/170 |
| 6,081,741 A | 6/2000 | Hollis | |
| 6,096,042 A * | 8/2000 | Herbert | B23B 49/006 606/80 |
| 6,342,057 B1 | 1/2002 | Brace et al. | |
| 6,494,590 B1 * | 12/2002 | Paganini | B25F 5/021 362/109 |
| 6,527,778 B2 * | 3/2003 | Athanasiou | A61B 10/0233 606/80 |
| 6,587,184 B2 | 7/2003 | Wursch et al. | |
| 6,665,948 B1 * | 12/2003 | Kozin | A61B 17/1626 175/45 |
| 6,786,683 B2 * | 9/2004 | Schaer | B23B 49/006 408/16 |
| D502,798 S | 3/2005 | Belley et al. | |
| 6,925,725 B2 * | 8/2005 | Herrmann | B21J 15/10 33/638 |
| 7,073,989 B2 * | 7/2006 | Erickson | B23B 45/003 408/112 |
| 7,185,998 B2 * | 3/2007 | Oomori | B25B 23/18 362/119 |
| 7,220,088 B2 | 5/2007 | Ferrari et al. | |
| 7,235,940 B2 * | 6/2007 | Bosch | B25B 23/147 173/4 |
| 7,314,048 B2 | 1/2008 | Couture et al. | |
| 7,482,819 B2 * | 1/2009 | Wuersch | B23B 49/006 173/6 |
| 7,578,642 B2 * | 8/2009 | Fritsche | B23Q 1/28 227/110 |
| 7,681,659 B2 * | 3/2010 | Zhang | B25B 21/00 173/1 |
| 7,691,106 B2 | 4/2010 | Schenberger | |
| 7,840,253 B2 | 11/2010 | Tremblay | |
| 7,946,049 B1 * | 5/2011 | Wilton | E04F 21/0092 33/526 |
| 7,992,311 B2 * | 8/2011 | Cerwin | B25H 1/0092 33/286 |
| 8,092,457 B2 | 1/2012 | Oettinger | |
| 8,162,074 B2 * | 4/2012 | Cook | B25F 5/021 173/1 |
| 8,167,518 B2 * | 5/2012 | Mathis | B23Q 5/225 408/1 R |
| 8,171,642 B2 * | 5/2012 | Fritsche | B23Q 1/621 29/897.2 |
| 8,317,437 B2 * | 11/2012 | Merkley | G05B 19/4163 408/9 |
| 8,460,297 B2 | 6/2013 | Watlington | |
| 8,511,945 B2 | 8/2013 | Apkarian | |
| 8,734,153 B2 * | 5/2014 | Arzanpour | A61C 1/0007 433/114 |
| 8,821,493 B2 * | 9/2014 | Anderson | A61B 90/06 606/80 |
| 8,894,654 B2 * | 11/2014 | Anderson | B25B 21/002 606/80 |
| 8,925,169 B2 * | 1/2015 | Schevers | B23B 49/00 29/407.08 |
| 8,970,207 B2 * | 3/2015 | Baumgartner | G01D 5/145 324/207.2 |
| 9,022,949 B2 | 5/2015 | Herndon | |
| 9,114,494 B1 * | 8/2015 | Mah | B25H 1/0092 |
| 9,204,885 B2 * | 12/2015 | McGinley | A61B 17/162 |
| 9,358,016 B2 * | 6/2016 | McGinley | A61B 17/1628 |
| 9,370,372 B2 * | 6/2016 | McGinley | A61B 17/162 |
| 9,492,181 B2 * | 11/2016 | McGinley | A61B 17/162 |
| 9,826,984 B2 | 11/2017 | McGinley | |
| 9,855,060 B2 | 1/2018 | Ardel | |
| 10,321,920 B2 * | 6/2019 | McGinley | A61B 17/1633 |
| 2001/0031919 A1 | 10/2001 | Strommer | |
| 2001/0047219 A1 * | 11/2001 | Oden | B23Q 17/12 700/159 |
| 2002/0165549 A1 | 11/2002 | Owusu-Akyaw et al. | |
| 2003/0049082 A1 * | 3/2003 | Morrison | B23B 49/026 408/56 |
| 2003/0229351 A1 | 12/2003 | Tidwell | |
| 2004/0146367 A1 * | 7/2004 | Gerhardt | B25F 5/003 408/110 |
| 2004/0179829 A1 * | 9/2004 | Phillips | H02P 29/02 388/804 |

(56) References Cited

U.S. PATENT DOCUMENTS

| | | | | |
|---|---|---|---|---|
| 2004/0215395 A1* | 10/2004 | Strasser | B23B 49/006 | 702/9 |
| 2005/0116673 A1* | 6/2005 | Carl | A61B 17/1626 | 318/432 |
| 2005/0131415 A1* | 6/2005 | Hearn | A61B 17/8875 | 606/80 |
| 2005/0169717 A1* | 8/2005 | Field | E21B 47/04 | 408/13 |
| 2005/0261870 A1* | 11/2005 | Cramer | B25H 1/0092 | 702/166 |
| 2006/0004371 A1 | 1/2006 | Williams et al. | | |
| 2006/0008771 A1* | 1/2006 | Courvoisier | A61B 17/1615 | 433/165 |
| 2006/0025677 A1 | 2/2006 | Verard | | |
| 2006/0074292 A1 | 4/2006 | Thomson | | |
| 2006/0241628 A1 | 10/2006 | Parak | | |
| 2006/0258938 A1 | 11/2006 | Hoffman | | |
| 2007/0030486 A1* | 2/2007 | Gelbart | G01B 11/27 | 356/399 |
| 2007/0035311 A1* | 2/2007 | Wuersch | B23B 49/006 | 324/644 |
| 2007/0041799 A1 | 2/2007 | Schaefer | | |
| 2008/0119725 A1 | 5/2008 | Lloyd | | |
| 2008/0167653 A1 | 7/2008 | Watlington | | |
| 2008/0226409 A1 | 9/2008 | Hasenzahl | | |
| 2008/0228195 A1 | 9/2008 | von Jako | | |
| 2008/0243125 A1 | 10/2008 | Guzman | | |
| 2008/0292416 A1 | 11/2008 | Kado et al. | | |
| 2009/0131986 A1 | 5/2009 | Lee et al. | | |
| 2009/0182226 A1 | 7/2009 | Weitzner | | |
| 2009/0245956 A1* | 10/2009 | Apkarian | A61B 34/30 | 408/1 R |
| 2009/0299439 A1* | 12/2009 | Mire | A61B 17/1671 | 607/60 |
| 2009/0326537 A1* | 12/2009 | Anderson | A61B 17/17 | 606/80 |
| 2010/0114099 A1 | 5/2010 | Patwardhan | | |
| 2010/0137874 A1* | 6/2010 | Kim | G01B 3/28 | 606/102 |
| 2010/0239380 A1 | 9/2010 | Amirov et al. | | |
| 2011/0020084 A1 | 1/2011 | Brett | | |
| 2011/0060242 A1* | 3/2011 | Hausman | A61B 17/1626 | 600/554 |
| 2011/0245831 A1 | 10/2011 | Giersch et al. | | |
| 2011/0245832 A1 | 10/2011 | Giersch et al. | | |
| 2011/0245833 A1* | 10/2011 | Anderson | B23B 45/008 | 606/80 |
| 2011/0301611 A1* | 12/2011 | Garcia | B25B 23/147 | 606/80 |
| 2012/0037386 A1* | 2/2012 | Cook | B25F 5/021 | 173/30 |
| 2012/0123418 A1 | 5/2012 | Giurgi | | |
| 2012/0179070 A1 | 7/2012 | Pommer et al. | | |
| 2012/0253348 A1 | 10/2012 | Arlettaz et al. | | |
| 2013/0122466 A1 | 5/2013 | Connor | | |
| 2013/0237811 A1 | 9/2013 | Mihailescu | | |
| 2013/0304069 A1* | 11/2013 | Bono | A61B 17/1624 | 606/80 |
| 2013/0307529 A1* | 11/2013 | Baumgartner | B23B 49/00 | 324/207.2 |
| 2013/0327552 A1 | 12/2013 | Lovelass | | |
| 2014/0039517 A1 | 2/2014 | Stryker | | |
| 2014/0081659 A1 | 3/2014 | Nawana | | |
| 2014/0107471 A1* | 4/2014 | Haider | A61B 1/3132 | 600/424 |
| 2014/0275760 A1 | 9/2014 | Lee | | |
| 2014/0275989 A1 | 9/2014 | Jacobsen | | |
| 2014/0350685 A1 | 11/2014 | Bagga | | |
| 2015/0066030 A1* | 3/2015 | McGinley | A61B 17/1628 | 606/79 |
| 2015/0066035 A1* | 3/2015 | McGinley | A61B 90/30 | 606/80 |
| 2015/0066036 A1* | 3/2015 | McGinley | A61B 17/162 | 606/80 |
| 2015/0066037 A1* | 3/2015 | McGinley | A61B 17/16 | 606/80 |
| 2015/0066038 A1* | 3/2015 | McGinley | A61B 17/1615 | 606/80 |
| 2015/0165580 A1* | 6/2015 | Holland | B25F 5/021 | 408/1 BD |
| 2016/0120553 A1* | 5/2016 | Xie | A61B 17/162 | 606/80 |
| 2016/0247276 A1 | 8/2016 | Chou | | |
| 2017/0128081 A1* | 5/2017 | McGinley | A61B 17/1626 | |
| 2017/0143396 A1* | 5/2017 | McGinley | A61B 90/06 | |
| 2017/0245868 A1 | 8/2017 | McGinley | | |
| 2017/0345398 A1 | 11/2017 | Fuchs | | |
| 2018/0070113 A1 | 3/2018 | Phillips | | |
| 2018/0110572 A1 | 4/2018 | Flatt | | |
| 2018/0260931 A1 | 9/2018 | Ozguner | | |
| 2019/0209287 A1 | 7/2019 | Zens-Olson | | |
| 2019/0254685 A1* | 8/2019 | McGinley | A61B 17/32002 | |

FOREIGN PATENT DOCUMENTS

| | | |
|---|---|---|
| WO | 2015006296 | 1/2015 |
| WO | 2015014771 | 2/2015 |
| WO | 2015034562 | 3/2015 |
| WO | 2016207628 A1 | 12/2016 |

* cited by examiner

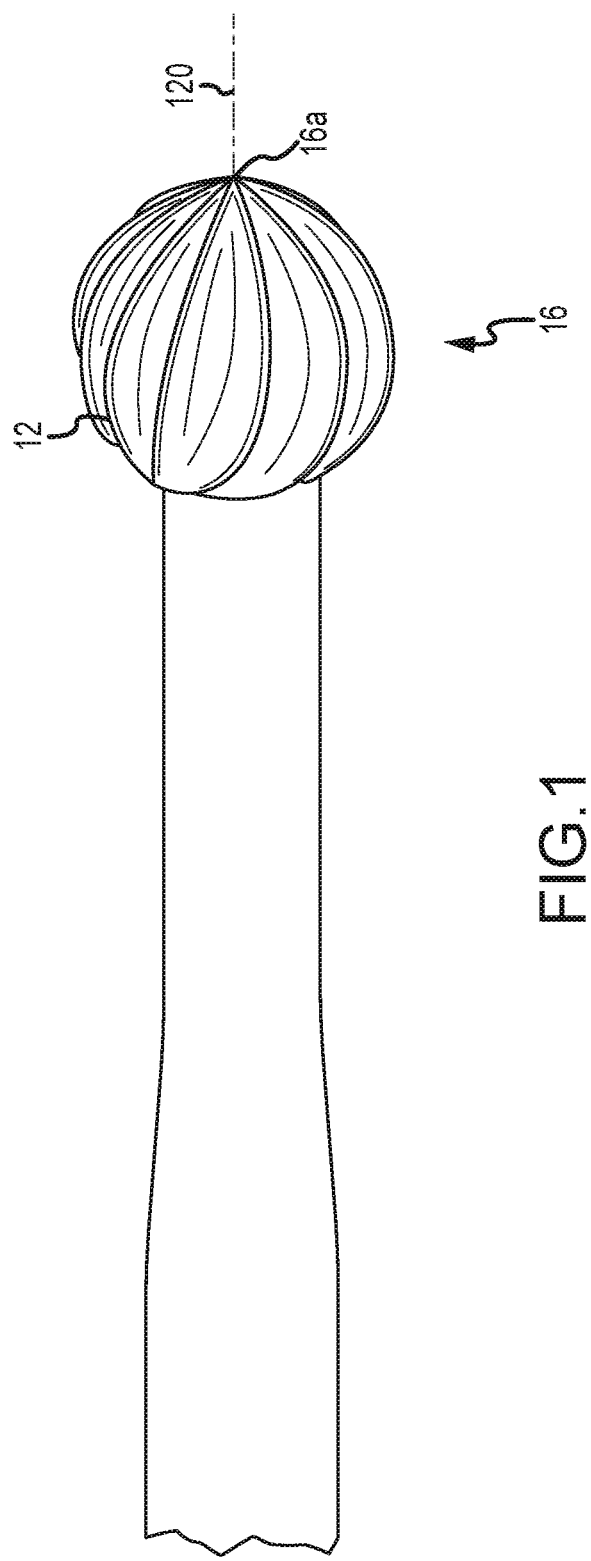

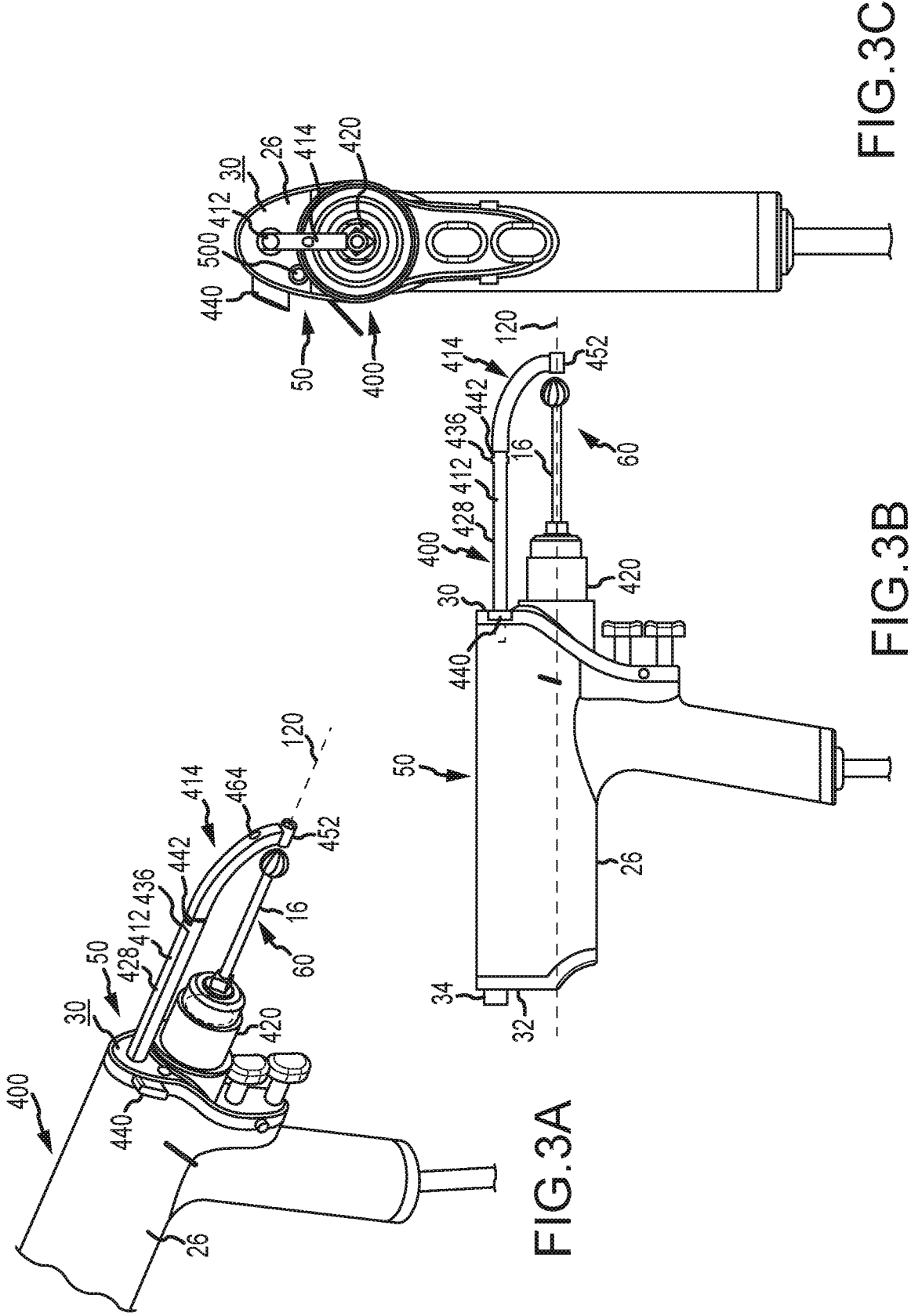

MEASUREMENT SYSTEM FOR USE WITH SURGICAL BURR INSTRUMENT

RELATED APPLICATIONS

This application is a division of U.S. application Ser. No. 15/330,825 filed on Nov. 7, 2016, entitled "MEASUREMENT SYSTEM FOR USE WITH SURGICAL BURR INSTRUMENT," which claims the benefit of U.S. Provisional Patent Application No. 62/252,193 filed Nov. 6, 2015, entitled "MEASUREMENT SYSTEM FOR USE WITH SURGICAL BURR INSTRUMENT," which is incorporated herein by reference in its entirety.

BACKGROUND

Powered instruments are often used in surgical procedures, and especially in orthopedic procedures. For instance, such instruments are often used to perform operations on a bone of the patient. Examples of such operations including drilling, sawing, grinding, or the like. The objectives of such operations are many and may, for example, include for inserting an orthopedic appliance, shaping a bone, or other appropriate operations. As may be appreciated, powered tools may assist a surgeon in performing a surgical operation by speeding such operations. Improving the speed at which operations may occur may be beneficial to limit the duration of anesthesia for the patient and/or may assist in avoiding other complications.

Despite the assistance that powered tools may provide, control of such instruments may be more difficult than hand-powered tools. In turn, unintended contact of the instrument with surrounding tissue (e.g., soft tissue surrounding the bone on which the operation is to occur) may cause damage to such surrounding tissue. In turn, reducing the risk of such unintended contact of the instrument with tissue may assist in improving surgical outcomes.

SUMMARY

In view the foregoing, a measurement system may be used with an instrument for use in connection with operation of an instrument. A detection module may be provided in operative communication with the measurement system to measure one or more parameters measured by the measurement system. The detection module may arrest the instrument to help reduce the possibility of damaging tissue surrounding a bone on which the instrument operates. For example, U.S. Pat. No. 6,665,948, U.S. Pat. Pub. No. 2015/0066035, U.S. Pat. Pub. No. 2015/0141999, and U.S. application Ser. No. 14/845,602, all of which are incorporated by reference herein in their entirety, disclose various systems and approaches to monitoring a powered surgical instrument. However, such disclosures have conventionally been directed to the measurement of the position of a working portion of a tool relative to a bone of a patient. In turn, these contexts involve measurement of the depth of a bore created by a drill bit or arresting a working tool portion upon engagement of the working tool with a specific portion of the bone.

In the present disclosure, the instrument may comprise a powered burr tool for use in grinding a bone. The burr tool may be used to bore into a bone in a manner similar to a drill as described in the disclosures incorporated by reference above. Additionally or alternatively, a burr tool may be used on a surface of a bone to grind a portion thereof. That is, the burr tool may be advanced radially relative to an axis of rotation of the burr tool. However, when using a burr tool, it may be more likely that the bone substrate fails, resulting in release of the instrument from the bone. Furthermore, given that a burr tool may be used to operate on an exterior surface of a bone, the potential that the instrument may slip from the external surface may be increased.

As such, the disclosure presented herein includes use of an instrument (e.g., a burr tool or other instrument) to operate on a bone. Furthermore, a measurement system may be utilized to measure one or more parameters related to the movement of the burr tool. In turn, a detection module may be provided to monitor the one or more parameters and control the instrument in response thereto. As such, the detection module may help reduce the potential of surrounding tissue damage when using a burr tool to perform an operation (e.g., a grinding operation) on an exterior portion of a bone. For instance, given that the measurement system may be operative to measure an applied force and/or displacement of the tool relative to a reference point, the measurement system may be operative to detect an instance in which the instrument slips from (i.e., suddenly loses contact with) the bone. Upon detection of such slippage or loss of contact, the instrument may be arrested to prevent and/or limit damage to surrounding tissue. Furthermore, the burr tool may be arrested upon completion of an operation relative to the bone (e.g., whether performed unicortically or bicortically).

As such, the measurement system may include a displacement sensor, acceleration sensor, and/or a force sensor that may be utilized to monitor the instrument. A detection module may monitor for an acceleration that exceeds a threshold or a force acting on the burr tool is reduced relative to a threshold (e.g., that may be indicative that the instrument has slipped). The instrument may be arrested upon completion of such an operation. In another context, the measurement system may be able to detect rapid accelerations of the instrument (e.g., using the displacement sensor). These rapid accelerations may result from the instrument slipping from the bone. As such, detection of such rapid acceleration may also cause the instrument to arrest to prevent damage surrounding tissue.

Furthermore, the burr instrument may have a predetermined ramp-up speed in which the angular velocity of the burr instrument upon start up slowly accelerates along a ramp-up profile. This may assist in providing safety with the burr instrument to prevent unintentional contact of the burr instrument at high speed with soft tissue.

Accordingly, a first aspect relates to an instrument for use in a surgical operation. The instrument may include a drive system for rotationally driving a working tool engaged with the instrument about a working axis and a burr tool engaged with the instrument for rotation of the burr tool by the drive system about the working axis. The burr tool is contactably engageable with a medium. The instrument may also have a measurement system for monitoring the contactable engagement of the burr tool with the medium and a detection module in operative communication with the measurement system to detect a loss of the contactable engagement of the burr tool with the medium.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, the measurement system may include an accelerometer for detecting an acceleration of the burr tool relative to the medium. The accelerometer may include a displacement sensor for outputting a displacement measure of the burr tool relative to the medium and an acceleration value may be determined based on a second derivative of the displacement measure. Additionally or alternatively, the accelerometer may measure an acceleration of the instrument directly. In either regard, the detection module may detect the loss of the contactable engagement of the burr tool with the medium in response to the acceleration of the burr tool relative to the medium exceeding an acceleration threshold value.

In an embodiment, the acceleration threshold value may be a value that is selectable by a user of the instrument. The acceleration threshold value may include a maximum acceleration magnitude value. Alternatively, the acceleration threshold value may include a maximum rate of change of the acceleration of the burr tool.

In an embodiment, the measurement system may include at least one force sensor. The at least one force sensor may be arranged relative to the burr tool to measure a force acting axially along the working axis. Also, the at least one force sensor may be arranged relative to the burr tool to measure a force acting radially relative to the working axis.

In an embodiment, the detection module may detect the loss of the contactable engagement of the burr tool with the medium in response to a reduction in force acting on the burr tool exceeding a force threshold value. The force threshold value may include a maximum rate of change of force and a loss of the contactable engagement of the burr tool is detected upon the rate of change in the force acting on the burr tool exceeding the maximum rate of change.

In an embodiment, the drive system may be operative to initiate rotation of the working tool such that a rotational speed of the working tool increases along a defined acceleration profile. The defined acceleration profile may be linear. Moreover, upon detection of the loss of the contactable engagement of the burr tool with the medium by the detection module, the drive system may be deactivated. Also, the instrument may include a brake in operative communication with the drive system. In turn, upon detection of the loss of the contactable engagement of the burr tool with the medium, the brake is activated to cease rotation of the working tool.

A second aspect is directed to a method for the use of an instrument. The method includes operating an instrument to perform an operation relative to a bone of the patient by contacting a working portion of the instrument with the bone of the patient and monitoring the working portion of the instrument. The method also includes detecting a loss of contact between the working portion and the bone and arresting the instrument upon detection of the loss of contact between the working portion and the bone.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For instance, the monitoring may include measuring one or more parameter using a measurement system of the instrument. Specifically, the measurement system may include an acceleration sensor and the one or more parameters may be an acceleration of the working tool relative to the bone. The detecting may include measuring the acceleration of the working tool relative to a bone that exceeds an acceleration threshold value.

Additionally or alternatively, the measurement system may include a force sensor and the one or more parameters may be a change in force acting on the working tool. In turn, the detecting may include measuring the change in force acting on the working tool that exceeds a force threshold value comprising a maximum rate of change in force.

The arresting may include ceasing operation of a drive system of the instrument. Additionally or alternatively, the arresting may include applying a brake to a drive system of the instrument.

A third aspect is directed to a method of use of a powered surgical burr tool. This method includes initiating rotation of the burr tool with the instrument. Specifically, the rotation of the burr tool accelerates according to an acceleration profile such that the full speed of the burr tool is delayed by a known time after the initiating.

BRIEF DESCRIPTION OF THE FIGURES

FIG. 1 depicts an embodiment of a working portion of a burr tool.

FIGS. 3A-3C depict various views of an embodiment of an instrument having a measurement system that may be used with a burr tool.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

As described above, the present disclosure generally relates to an instrument 50 such as that shown in the figures. The instrument 50 may be a powered surgical instrument such as a drill, saw, reciprocating tool, or the like. In one embodiment, the instrument 50 may be engaged with a burr tool 16 like the one shown in FIG. 1. The burr tool 16 may include a working portion 12 that may have fluted or ridged portions. The working portion 12 may allow for abrading or grinding a bone or other calcified or hardened substrate. As such, it may be appreciated the burr tool 16 may be used in a context similar to a drill bit, where the burr tool 16 is advanced axially along a working axis 120 about which the burr tool 16 is rotated. Additionally or alternatively, the burr tool 16 may be used to grind by advancing the burr tool 16 in a direction perpendicular to the working axis 120. Moreover, a combination of radial and axial movement may also be used and monitored as described in greater detail below.

In this regard, as has been described in U.S. Pat. No. 6,665,948, U.S. Pat. Pub. No. 2015/0066035, U.S. Pat. Pub.

No. 2015/0141999, and U.S. application Ser. No. 14/845, 602, all of which are incorporated by reference above, various methodologies and approaches to monitoring a tool as it is advanced bicortically or unicortically through a bone of a patient. In this regard, in the event the burr tool 16 is utilized in a manner similar to a drill bit where the burr tool 16 is advanced to create a bore in the bone, any of the methodology or structure utilized in the references incorporated therein may be used in conjunction with the burr tool 16. That is, the burr tool 16 may stand in the place of any tool, instrument, or drill bit described in any of the incorporated disclosure. As such, as shown in FIGS. 2A, 2B, 3A, 3B, 3C, 4, and 5, the burr tool 16 may be used with any type of measurement system described in the incorporated references. As such, the burr tool 16 may be used to create a bore. Upon the burr tool 16 passing through a bone or a portion of a bone, the instrument driving the burr tool 16 may be arrested. This may prevent unintended damage to tissue surrounding the bone when using the burr tool 16.

Figure 2A:
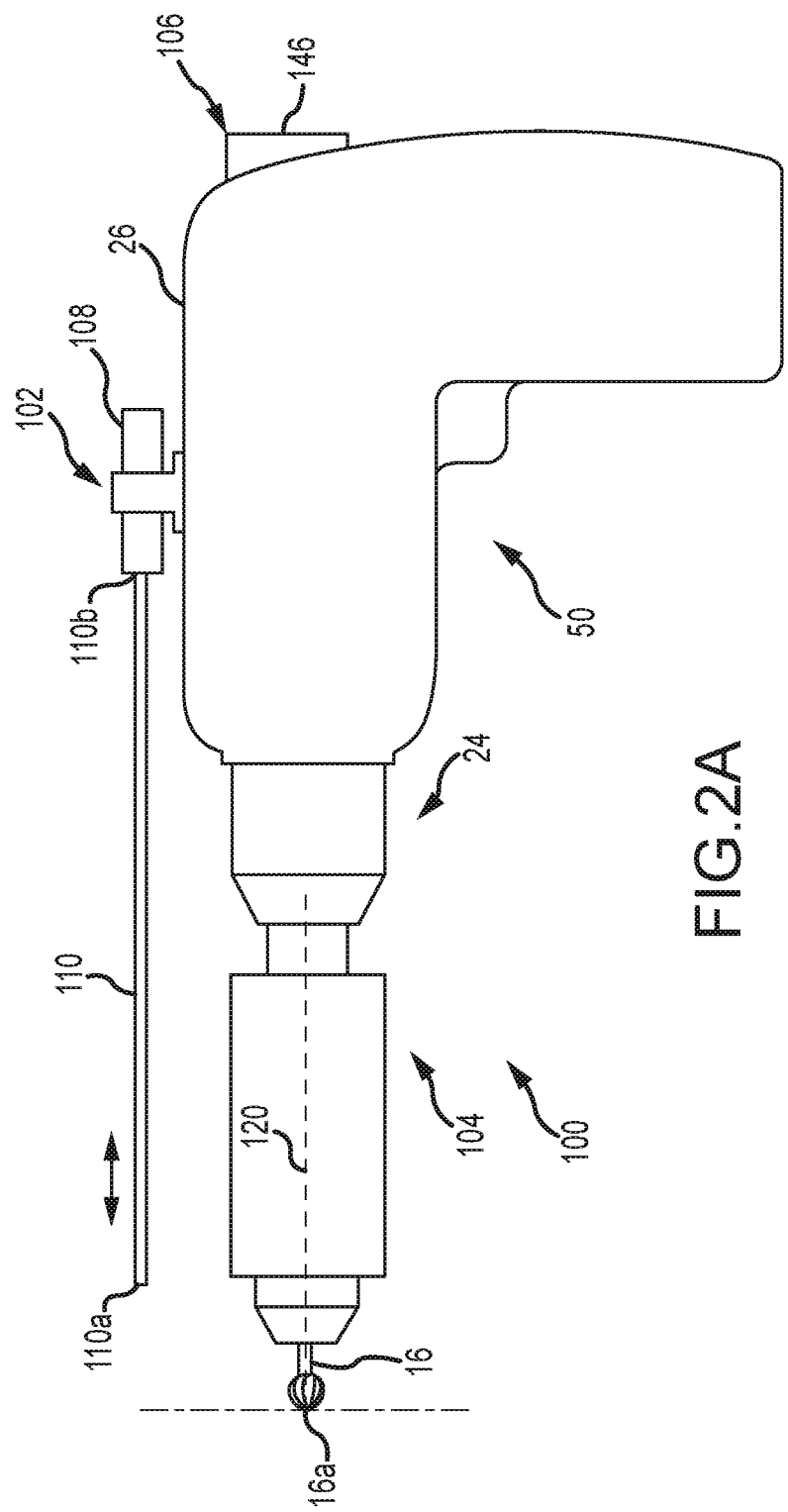
FIG. 2A depicts an embodiment of an instrument having a measurement system that may be used with a burr tool.
Figure 2B:
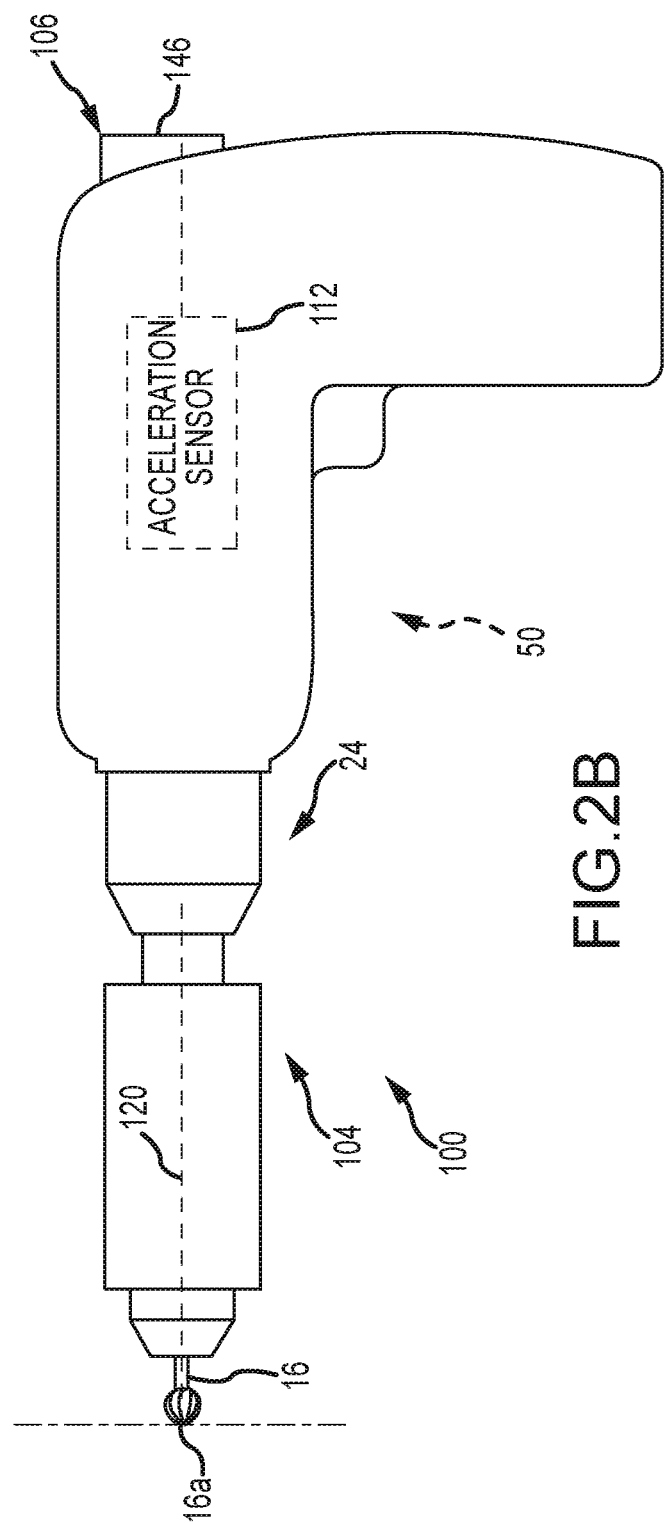
FIG. 2B depicts an embodiment of an instrument having a measurement system that may be used with a burr tool.

Referring to FIGS. 2A and 2B, an instrument 50 may include a measurement system 100 that comprises a displacement sensor 102, a force sensor 104, and a controller assembly 106. The displacement sensor 102 may be connected to the instrument housing 26. The connection can be made by a variety of well-known mounting methods such as a mount that clamps to the displacement sensor 102 and is attached to the instrument housing 26 by one or more threaded fasteners. Alternative methods such as welding or adhesive bonding could also be used.

The displacement sensor 102 may include a transducer 108 that outputs a displacement signal that is representative of a displacement, with respect to the reference point, of the leading edge 16a of the burr tool 16. The displacement sensor 102 may have an extension 110 that is displaceable along a longitudinal axis. The extension 110 has a distal end 110a that can be placed in registry with the reference point when the leading edge 16a of the burr tool 16 is positioned relative to a bone (e.g., placed in contact therewith). The distal end 110a may be maintained in registry with the reference point throughout the process conducted using the burr tool 16. The reference point can be any anatomical structure proximal to the location at which the burr tool 16 is used. The extension 110 has a proximal end 110b that is attached to the first sensor 102. Preferably the transducer 102 is a linear variable differential displacement transducer ("LVDT").

Furthermore, it may be appreciated that the spacing of the extension 110 of the displacement sensor 102 from the burr tool 16 may introduce the potential for errors or other disadvantages in determining the displacement of the burr tool 16 relative to the reference point. For instance, as the extension 110 may contact a structure that is offset from the contact point between the leading edge 16a of the burr tool 16 and the medium to be subjected to an operation using the burr tool 16. Accordingly, any movement between the structure contacted by the extension 110 and the medium on which the burr tool 16 is used may be falsely registered as relative movement of the burr tool 16 with respect to the reference point. Furthermore, there may not be a rigid structure to contact adjacent to the medium to be contacted, leading to displacement of the structure contacted by the extension 110 (e.g., such as in the case where the extension 110 may contact soft tissue adjacent to the medium to be contacted given the offset from the location to be contacted). Furthermore, the offset nature of the extension 110 relative to the contact between the burr tool 16 and the medium to be contacted may lead to other complications such as having to expose a greater surface of the medium to be contacted, which may adversely affect patient outcomes.

In this regard, and with further reference to FIG. 2B, an embodiment of an instrument 50 may be provided that includes an acceleration sensor 112. An acceleration sensor 112 may be provided as an alternative to or in addition to the displacement sensor 102 described above. The acceleration sensor 112 may be a MEMS accelerometer, an optical accelerometer, a piezoelectric accelerometer, or any other appropriate accelerometer. In turn, the acceleration sensor 112 may be operative to determine an acceleration of the instrument 50, which may be rigidly interconnected with the burr tool 16. As such, an acceleration of the burr tool 16 may be sensed by the acceleration sensor 112.

Further still, in either of the embodiments of an instrument 50 depicted in FIG. 2A or 2B may include a force sensor 104. Specifically, the working portion load measurement assembly 104 may include one or more force sensors. The one or more force sensors may be arranged to measure a force applied to the burr tool 16 when in use. A force sensor element may be arranged to measure an axial load acting on the burr tool 16 that results in advancement of the burr tool 16 as the burr tool 16 is advanced axially relative to the working axis 120. In addition, one or more force sensor elements may be provided that are arranged to measure a force acting in a radial direction relative to the working axis 120. In this regard, in a grinding operation where the burr tool 16 is advanced in a direction radial to the working axis 120, a force acting on the burr tool 16 may be monitored. In turn, monitoring of the force acting on the burr tool 16 (e.g., either axially or radially) may assist in determining unintended slippage of the burr tool 16 as will be discussed in greater detail below.

Another embodiment of an instrument with a displacement sensor including a displacement sensing arm that extends from the instrument may be provided. For example, such a displacement sensing arm may be provided that may coordinate with a bushing member of a burr tool assembly that may be used with the instrument. In this regard, the bushing may move along the burr tool in a direction corresponding to the axis of rotation of the burr tool. Upon engagement of the bushing and the displacement sensing arm, the bushing and displacement sensing arm may undergo corresponding movement. As such, the bushing may be disposed in contact with the medium to be contacted when the leading edge of the burr tool is in contact with the medium. As such, a reference point may be established when the bushing and leading edge of the burr tool are both in contact with the medium to be contacted by the burr tool. As the bushing is located adjacent to (e.g., partially or fully surrounding the burr tool), the bushing may facilitate contact with the medium at or very near the location to be contacted prior to initiation of an operation using the burr tool. In this regard, the reference point may be more accurately maintained as the bushing may contact at least a portion of a periphery of the bone adjacent to where the burr tool is used to remove tissue. That is, the bushing may remain in intimate contact with the medium to be contacted adjacent to the burr tool. This may prevent false displacement readings attributable to the foregoing problems associated with an offset extension 110. Furthermore, the amount of contact of the bushing may be localized at the location to be contacted by the burr tool, thus allowing for potentially less intrusion when performing operations using the burr tool.

For example, with additional reference to FIGS. 3A, 3B, 3C, and 4, an embodiment of an instrument 50 comprising an embodiment of a measurement system 400 is shown. The instrument 50 may be adapted for use with a burr tool assembly 60 (shown in FIG. 5) that may include a bushing 452. The instrument 50 may integrally comprise at least some components of the measurement system 400 to facilitate operation of the measurement system 400 in connection with the instrument 50 (e.g., which may be according to the description above regarding measurement system 100). For example, at least a portion of a displacement sensor 410 may be integrated into a housing 26 of the instrument 50. In this regard, the displacement sensor 410 may include a depth sensing arm 412 that is specifically adapted for engagement with a bushing 452 of a burr tool assembly 60 that may be engaged by the chuck 420 of the instrument 50.

In this regard, the depth sensing arm 412 may be used to establish a reference point from which displacement of the burr tool 16 may be measured as described above. In this regard, as follows herein, a general description of the features and operation of the instrument 50 used in conjunction with the burr tool assembly 60 is provided.

The displacement sensor 410 may include a depth sensing arm 412 that may extend from the instrument housing 26. For example, the depth sensing arm 412 may extend distally (e.g., from a distal face 30 of the instrument 26) in a direction corresponding with the direction in which the burr tool 16 extends from a chuck 420 of the instrument 50. As such, the chuck 420 may engage the burr tool 16. At least a portion of the displacement sensing arm 412 may extend from the instrument housing 26 parallel to an axis of rotation 120 of the instrument 50. The depth sensing arm 412 may also include a distal portion 414 that is adapted to engage a bushing 452 provided with the burr tool assembly 60 shown in FIG. 4. As used herein, distal may correspond to a direction from the instrument 50 toward the leading edge 16a of the burr tool 16 and proximal may correspond to a direction from the leading edge 16a of the burr tool 16 toward the rear portion of the instrument 50. In this regard, at least a portion of the depth sensing arm 412 (e.g., the distal portion 414) may be adapted to engage the bushing 452 of the burr tool assembly 60 as will be described in more detail below. In any regard, at least a portion of the depth sensing arm 412 may extend into the housing 26. The housing 26 may contain a coil 416. As such, a proximal end 418 of the displacement sensing arm 412 may interface with the coil 416 of the displacement sensor 410 that may be disposed within the instrument housing 26.

Figure 4:
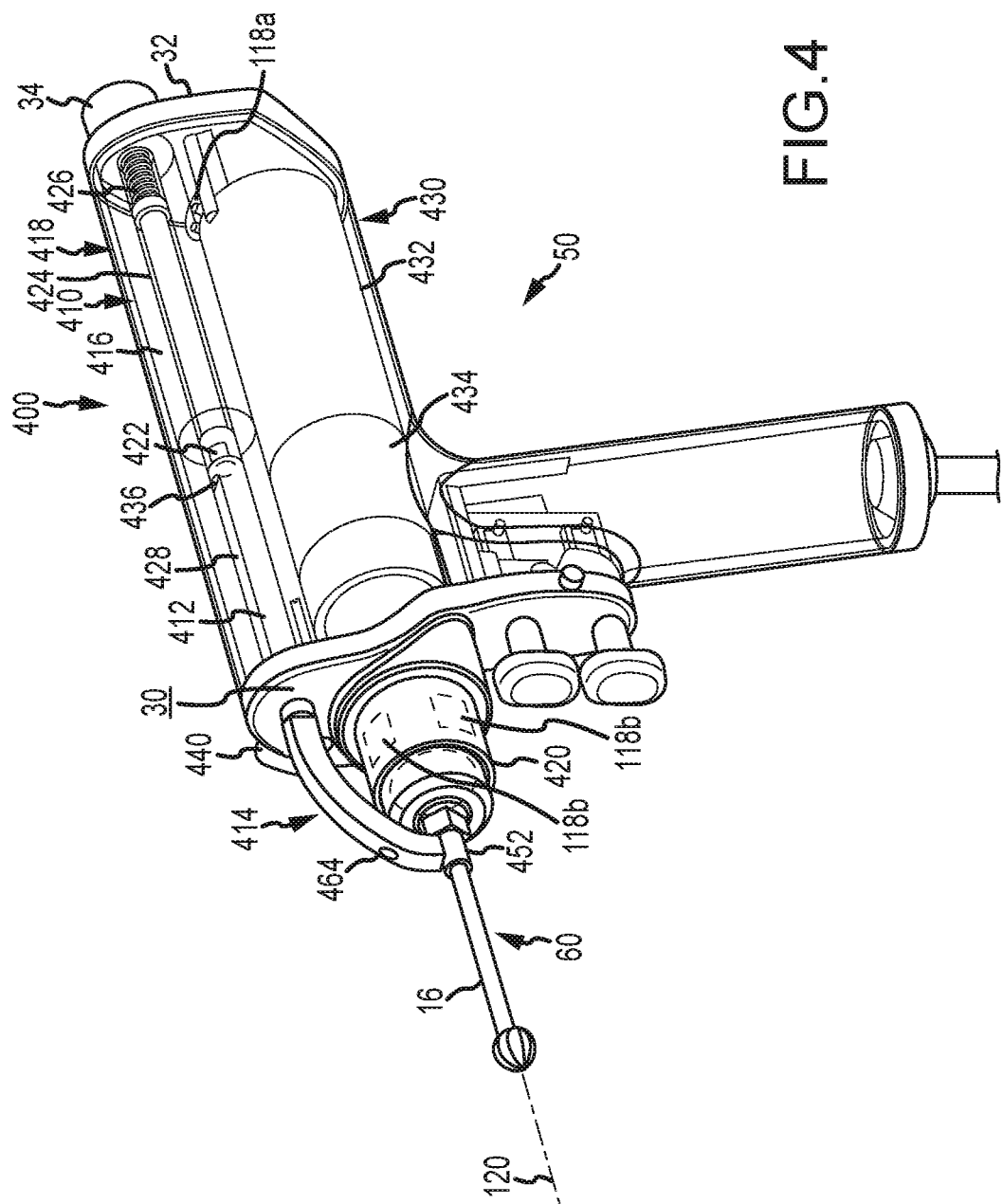
FIG. 4 depicts an embodiment of an instrument having a measurement system with a housing thereof not shown for clarity.

Specifically, in FIG. 4, the depth sensing arm 412 is shown in a retracted position relative to the burr tool 16. As such, this retracted position shown in FIG. 11 may occur when the burr tool 16 is advanced relative to the bushing 452 during an operation. In this regard, the proximal end 418 of the displacement sensing arm 412 is disposed within the coil 416 of the displacement sensor 410. Accordingly, the displacement sensor 410 may comprise an LVDT sensor as described above that is adapted to sense the position of a core 422 relative to a coil 416. The displacement sensing arm 412 may incorporate a core 422 at the proximal end 418 thereof. Accordingly, as the proximal end 418 of the displacement sensing arm 412 is moved relative to the coil 416, the location of the core 422 may be determined to provide an output corresponding to the position of the core 422, and in turn the displacement sensing arm 412 relative to the instrument housing 26. That is, the depth sensing arm 412 may be displaceable relative to the coil 416 such that the displacement sensor 410 may be operable to sense a change in position of the depth sensing arm 412 relative to the instrument housing 26 and output a measure of the displacement of the burr tool relative to a reference point. In an embodiment, the total measurable travel of the core 422 relative to the coil 416 may be at least about 2.5 in (6.4 cm). Furthermore, the resolution of the output of the displacement sensor 410 may be about 0.1% (e.g., about 0.002 inches (0.06 mm) for a sensor having a total measurable travel of 2.5 inches).

While an LVDT displacement sensor is shown and described in relation to the instrument 50 shown in the accompanying figures, it may be appreciated that other types of displacement sensors may be provided. For instance, the sensor may provide for the absolute or relative measurement of the position of the distal end 418 of the displacement sensing arm 412 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure.

In an embodiment, the coil 416 may define a passage 424 extending at least partially through the housing 26. Specifically, the passage 424 may extend from a proximal face 32 of the housing 26 to the distal face 30 of the housing 26. That is, the passage 424 may extend entirely through the housing 26. An end cap 34 may be provided that is operable to close the proximal end of the passage 424 at the proximal face 32 of the instrument housing 26. Furthermore, a biasing member 426 (e.g., a coil spring) may be provided in the passageway 424 at a proximal end thereof. The biasing member 426 may be provided between the end cap 34 and the proximal end 418 of the displacement sensing arm 412. In this regard, the biasing member 426 may act on the proximal end 418 of the displacement sensing arm 412 to bias the displacement sensing arm 412 distally relative to the passage 424 and instrument housing 26.

As such, the displacement sensing arm 412 may include features that selectively prevent ejection of the displacement sensing arm 412 from the distal end of the passage 424. For example, the displacement sensing arm 412 may include at least one flat 428 that extends along a portion of the arm 412. At the proximal and distal extents of the flat 428, the displacement sensing arm 412 may include shoulders 436 that project from the flats 428. As such, at the proximal opening of the passage 424, a selectively displaceable stop 438 (best seen in FIG. 23) may be disposed relative to the flat 428 such that the flat 428 may move relative to the stop 438, but interfere with the shoulder 436 defined in the displacement sensing arm 412 to prevent passage of the shoulder 436 beyond the stop 438. In this regard, the length of the displacement sensing arm 412 along which the flat 428 extends may be moveable relative to the stop 438, and the stop 438 may limit proximal and distal movement of the displacement sensing arm 412 beyond the stop 438.

However, the stop 438 may be displaceable upon depressing a button 440 provided on an exterior of the housing 26. Other types of actuators may be used to control the stop 438 and a button 440 is provided as merely one example. Thus, upon depressing the button 440, the stop 438 may be displaced away from the displacement sensing arm 412 to allow the shoulder 436 to pass distally from the distal end of the passage 424 such that the displacement sensing arm 412 may be removed entirely from the passage 424. The distal end of the flats 438 may include a detent 442 that may be engageable with the stop 438 so as to maintain the displacement sensing arm 412 in a proximally disposed, retracted position relative to the housing (e.g., as shown in FIG. 4). Once the button 440 is depressed and released, the detent 442 at the proximal end of the flat 428 of the displacement sensing arm 412 may be released by the stop 438 and the displacement sensing arm 412 may move proximally (e.g., under influence of the biasing member 426). The displacement sensing arm 412 may move proximally until the shoulder 436 at the distal end of the flat 428 are engaged to prevent further distal movement of the displacement sensing arm 412. Accordingly, the displacement sensing arm 412 may be retained in a retracted position (e.g., for improved visibility of the distal end of the burr tool 16), released to be moveable relative to and biased proximally with respect to the housing 26, and removable altogether from the housing 26.

In the latter regard, removal of the displacement sensing arm 412 and biasing member 426 from the passage 424 may allow for separate cleaning (e.g., in an autoclave) of those members. Additionally, removal of the end cap 34 may allow for a cleaning apparatus (e.g., a brush or the like) to be passed through the full length of the passage 424 to facilitate cleaning thereof.

As referenced above, the distal portion 414 of the displacement sensing arm 412 may be adapted to engage a burr tool assembly 60 (e.g., a bushing 452 thereof) that is correspondingly adapted for use with the instrument 50. For instance, the displacement sensing arm 412 may generally be linear along the proximal portion 418 of the displacement sensing arm 412. In this regard, the proximal portion 418 may be adapted to be collinear with the passage 424 and moveable within the passage 424. Furthermore, the distal portion 414 of the displacement sensing arm 412 (e.g., the portion distal to the linear portion of the displacement sensing arm 412) may extend from the linear portion of the displacement sensing arm 412 toward the burr tool assembly 60 that may be engaged by the chuck 420 of the instrument 50. In this regard, the linear portion of the displacement sensing arm 412 may be substantially parallel to and offset from the axis of rotation 120. The distal portion 414 may extend from the linear portion in a direction corresponding with the offset such that the distal portion 414 extends toward the burr tool assembly 60. This may facilitate engagement between the displacement sensing arm 412 and the bushing 454 of the burr tool assembly 60. As shown, in FIGS. 3A-4, the distal portion 414 may be an at least partially arcuate member extending along a radius of curvature toward the burr tool assembly 60. However, the distal portion 414 may be shaped differently (e.g., the distal portion 414 may be a linear portion extending at an angle or perpendicularly from the proximal 418 toward the burr tool assembly 60).

Figure 5:
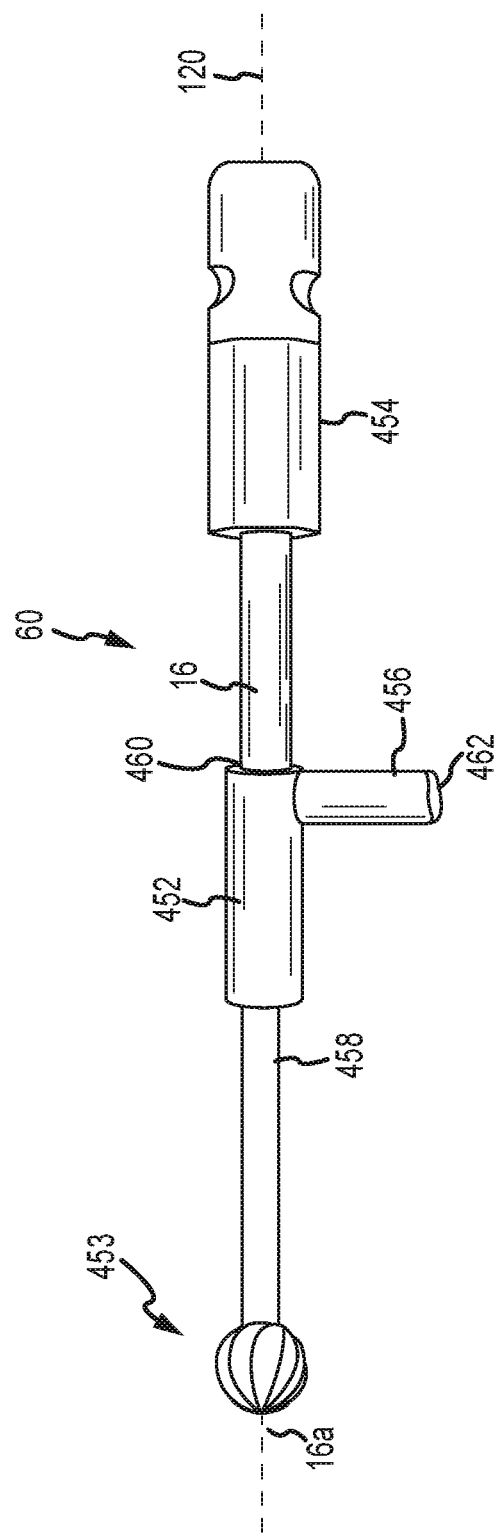
FIG. 5 depicts an embodiment of a burr tool assembly.

With further reference to FIG. 5, an embodiment of a burr tool assembly 60 that may be used in conjunction with the instrument 50 is depicted. The burr tool assembly 60 may include a shank 454 that is disposed adjacent to a proximal end of the assembly 60. There may be sharped fluted ridges disposed in a working portion 453 adjacent to the leading edge 16a of the burr tool assembly 16. These ridges may include cutting edges that, when rotated serves to abrade or grind the medium into which the burr tool 16 is advanced. In certain applications, the working portion 453 may be generally spherical. In other applications, the working portion 453 may be conical, ovoid, or any other appropriate shape. Moreover, the working portion 453 may be of any appropriate size for application in various different contexts in which the burr tool may be utilized. A cylindrical member 458 may extend between the shank 454 and the working portion 453. The working portion 453, cylindrical body 458, and shank 454 may collectively define the burr tool 16.

In addition to the burr tool 16, the burr tool assembly 60 may also comprise a bushing 452 as referenced above. The bushing 452 may engage the cylindrical member 458 to facilitate relative movement of the bushing 452 relative to the cylindrical member 458 along a direction corresponding to the axis of rotation 120. For example, the bushing 452 may include an aperture 460 through which at least a portion of the cylindrical member 458 may be disposed. The aperture 460 may form a cylindrical opening that extends at least in a direction corresponding to the axis of rotation 120 of the burr tool 16. The cylindrical opening may be sized to receive the cylindrical member 458 therein such relative movement between the cylindrical opening and the cylindrical member 458 is provided. Moreover, the bushing 452 may be sized so as to be operable to pass over the working portion 453. In this regard, the bushing 452 may surround the working portion 453 when the bushing is in a distal position such that the leading edge 16a of the working portion 453 is aligned axially with the distal edge of the bushing 453. As such, the burr tool 16 may be free to rotate within the aperture 460 (e.g., even when the bushing 452 is disposed about the working portion 453), and the bushing 452 may slideably engage the cylindrical member 458 for relative movement therebetween that is constrained along the direction corresponding to the axis of rotation 120. Further still, as the bushing member 452 may surround the working portion 453 when in a biased, distal position, the working portion 453 may be at least partially shielded to prevent unintended contact with surrounding tissue. Moreover, as the working portion 453 is advanced relative to the bone to be the target to an operation, the bushing 452 may be moved proximally relative to the working portion 453 so as to allow measurement of the displacement of the working portion 453. This may be particularly helpful in relation to monitoring the working portion 453 to detected unintended slippage that may otherwise lead to damage to the surrounding tissue.

The bushing 452 may include an engagement member 456 that is disposed on the bushing 452 and adapted for engagement with a displacement sensing arm 412 of an instrument 50 to which the burr tool assembly 60 is engaged. For instance, as depicted in FIG. 5, the engagement member 456 may comprise a post 462 extending from the bushing 452. The post 462 may extend away from the axis of rotation 120 of the burr tool assembly 60. In an embodiment, the post 462 may extend perpendicularly to the axis of rotation 120. Accordingly, the post 462 may engage a hole 464 provided on the distal portion 414 of the displacement sensing arm 412. In this regard, the post 462 may extend into the hole 464. Movement of the bushing 452 relative to the burr tool 16 in a direction corresponding to the axis of rotation 120 may result in the post 462 acting on the hole 464 such that the displacement sensing arm 412 undergoes corresponding movement upon movement of the bushing 452 relative to the burr tool 16. In turn, as described above, the core 422 at the proximal portion 418 the displacement sensing arm 412 may also undergo corresponding movement relative to the coil 416, which may be detected by the displacement sensor 410 and output as a displacement measure.

It may be appreciated that other arrangements for engaging the bushing 452 with the displacement sensing arm 412 may be provided so that the bushing 452 and displacement sending arm 412 undergo corresponding movement. For example, other structures such as clasps, fasteners, or other mechanisms may be utilized to engage the bushing 452 to the displacement sensing arm 412. Furthermore, the bushing 452 may, in some embodiments, be integrally defined on the distal portion 414 of the displacement sensing arm 412. In this regard, a standard burr tool 16 may be engaged with a chuck 420 of the instrument 50 and the bushing 452 may be disposed relative to the burr tool 16. In any regard, the bushing 452 may be pivotal relative to the displacement sensing arm 412 (e.g., in a direction perpendicular to the axis of rotation 120) to facilitate ease of engagement of the bushing 452 with the displacement sensing arm 412 or the bushing 452 with the burr tool 16 when engaging the burr tool 16 with the chuck 420 of the instrument 50.

In any regard, the shank 454 of the burr tool assembly 60 may be engaged with the chuck 420 of the instrument 50. In this regard, the burr tool 16 may be fixed relative to the instrument 50 in the direction along the axis of rotation 120. In turn, the bushing 452 may be displaceable relative to the burr tool 16 along the axis of rotation 120. In this regard, when the burr tool 16 is advanced relative to a medium during an operation, the bushing 452 may remain stationary at a reference point established prior to the operation and the displacement sensor 410 may be operable to detect the relative motion between the burr tool 16 and the bushing 452 retained in a stationary position relative to the reference point, thus providing a measure of the relative movement of the burr tool 16 relative to the reference point.

As may be appreciated, when using the instrument 50, a force sensor for measurement of force acting on the leading edge 16*a* of the burr tool 16 may also be provided. In this regard, a force sensor 118*a* (e.g., a force sensor such as piezoelectric crystal) may be disposed proximally to the instrument drive assembly 430 (which may include the chuck 420, gear drive 434, and motor 432). In turn, force acting on the leading edge 16*a* of the burr tool 16 as it is advanced axially may be transferred to the force sensor 118*a* via the drive system 430. That is, the axial force acting on the leading edge 16*a* of the burr tool 16 may be transferred through the shank 454 of the burr tool 16 to the chuck 420, and the drive system 430. In turn, the drive 430 may act upon the force sensor 118*a* to produce an output corresponding to the force acting on the leading edge 16*a*. In this regard, it may be appreciated that the rigid assembly of the drive 430, chuck 420, and burr tool 16 may transmit the force acting on the leading edge 16*a* of the burr tool 16 to the force sensor 118*a*. It may further be appreciated that the drive assembly 430 may be fixed rotationally relative to the instrument housing 26 so as to impart rotation to the chuck 420. However, the drive 430 may be preferably free to move in a direction along the axis of rotation 120 such that the at least a majority of the force acting on the leading edge 16*a* of the burr tool 16 may be transferred to the force sensor 118.

In addition to the force sensor 118*a* that is capable of measuring an axial force acting on the burr tool 16, a number of additional force sensors 118*b* may also be provided. These force sensors 118*b* may be arranged radially about the working axis 120. In turn, a force acting on the burr tool 16 in a direction radial relative to the working axis 120 may be measured by the force sensors 118*b*. As such, if the burr tool 16 is advanced in a radial direction (e.g., to perform a grinding operation or the like), the radial force acting on the burr tool 16 may also be measured.

In an embodiment, the force sensors 118*a* and 118*b* may have a range of measurable force from about 0 lbf (0 N) to about 100 lbf (445 N). In an embodiment, the force sensors 118*a* and 118*b* may have a range of measurable force from about 0 lbf (0 N) to about 25 lbf (111 N). The force sensors 118*a* and 118*b* may have a precision of at least about 1% of the maximum measurable force. Accordingly, in an embodiment, the force sensors 118*a* and 118*b* may have a precision of at least about 0.25 lbf (1.1 N). In an embodiment, the force sensors 118*a* and 118*b* may have a precision of 0.5% (e.g., about 0.125 lbf (0.56 N)).

As such, a displacement sensor (e.g., 102 or 40), an acceleration sensor 112, and/or one or more force sensors (e.g., 104 or 118*a* or 118*b*) may be provided with a measurement system used with a burr tool 16. As such, the various sensors may comprise a measurement system that may be used to monitor the burr tool 16 during operation. While the displacement and/or acceleration measured by the measurement system 40 may be used by the instrument 50 in conjunction with use of a burr tool 16 for creation of bore (e.g., to arrest the instrument upon passing through all or a portion of the bone), the measurement system 40 may also monitor the burr tool 16 during a grinding or boring operation. For instance, burr tools 16 may be used to shave a bone in the spine of a patient which may be conducted near blood vessels or nerves that may be damaged upon unintentional contact with the burr tool 16.

In this regard, the burr tool 16 may be used in a manner such that a working portion of the burr tool 16 is contacted with a medium (e.g., a bone of a patient). The contacting engagement may comprise advancing the burr tool 16 axially along the working axis 120, radially relative to the working axis 120, and/or a combination thereof. In turn, use of the burr tool may include risk that the burr tool 16 may slip from the bone or other hard structure being ground using the burr tool 16. Such loss of contact, which may be sudden) with the medium with which the burr tool 16 is in contact (which is also referred to herein as a slip) may increase the risk that surrounding tissue is inadvertently contacted by the working portion of the burr tool 16. This contact may cause damage to surrounding tissue, and is therefore preferably minimized.

In turn, a detection module may be in operative communication with the measurement system. The detection module may monitor for any such loss of contact or slippage and may arrest the instrument 50 upon detecting any such slippage. The instrument 50 may cease operation of a drive of the instrument and/or apply a brake to cease rotation of the instrument.

One or more of a number of parameters may be monitored by the detection module. In turn, slippage or sudden loss of contact of the burr tool 16 with a medium with which the burr tool 16 is in contact may be detected based on one or more of the parameters monitored by the detection module. Specifically, when the burr tool 16 slips, the burr tool 16 may experience an unexpected and relatively large acceleration. As the burr tool 16 may be monitored for displacement relative to a reference point and/or the acceleration of the instrument may be monitored by an acceleration sensor 112, the measurement system 40 may be operative to detect an acceleration of the burr tool 16. For instance, an acceleration may be detected by a dedicated acceleration sensor or may be derived from a measured displacement of the burr tool 16 relative to a reference point. In the latter case, a signal representative of displacement may be output by a displacement sensor. A derivative may be determined reflecting a rate of change of the displacement (e.g., a velocity). A second derivative of the displacement sensor may also be calculated that is indicative of an acceleration of the burr tool 16. In this regard, a displacement sensor along with a measurement system capable of processing the signal to arrive at an acceleration value may also be used as an acceleration sensor to determine an acceleration of a burr tool 16 for use in monitoring the burr tool 16 in a manner described herein.

Some minor accelerations may be associated with normal operations. As such, an acceleration threshold value may be established such that if the observed acceleration exceeds the acceleration threshold value, the instrument may be arrested. The acceleration threshold value may comprise a predetermined acceleration value. In other embodiments, the acceleration threshold value may be selectable by a user. Such an acceleration threshold value may comprise a magnitude of acceleration of the burr tool 16 and/or a value related to a maximum rate of change of the acceleration of the burr tool 16. As such, a measured acceleration magnitude that exceeds the acceleration threshold value (e.g., due to slippage of the instrument 50) may result in the instrument being arrested. This may prevent and/or limit damage to surrounding issue in the case of slippage. This monitoring may also occur during use of the burr tool 16 in an operation to create a bore. For instance, in the event of a bone failure or other fracture that result in slippage or other sudden acceleration, even in the case of creation of a bore, the instrument may be operative to arrest upon detection of such an acceleration to prevent and/or limit damage to surrounding tissue.

Furthermore, a slip of the instrument may also be accompanied by a decrease (e.g. a rapid decrease) in the force acting either axially or radially on the burr tool 16. In turn, a rapid deceleration (e.g., indicated by a rate of decrease in force above a given magnitude in force reduction or a rate of change in force) may indicate the burr tool 16 has slipped from the bone. That is, a force threshold value may be established. The force threshold value may comprise a detection of a decrease in force greater than a predetermined magnitude or a predetermined rate in change of force. In response, the instrument 50 may be stopped (e.g., by deactivating the drive and/or applying a brake) upon the measured force exceeding the force threshold value. However, a decrease in force that occurs below the force threshold value may not interrupt operation. Such a condition may be present when a user is still contacting a desired medium, but with a lesser force than previously applied. The force threshold value may be controllable by a user to assist in preventing false detection of a loss of contact or slip.

As such, a detection module may be provided in connection with a controller of the instrument 50. The detection module may monitor one or more signal provided from corresponding ones of one or more sensors (e.g., a displacement, acceleration, and/or force sensor). In response to one or more of the conditions described above, the detection module may be in operative communication with a drive control of the instrument to cease operation of the instrument and/or engage a brake to cease rotation of the instrument. The detection module may allow the predetermined thresholds for acceleration, rate of change in force, or other variables associated with monitoring of the instrument 50 to be adjusted.

The detection module may comprise any appropriate hardware, software, or combinations thereof. For instance, the module may be executed by a processor in operative communication with a memory that stores instructions for configuration of the processor to perform the monitoring and detection functions described above. In this regard, the processor may be in operative communication with a measurement system of an instrument. As such, the processor that executes the detection module may receive signals associated with displacement, acceleration, and/or force as described above. The processor may then apply rules in relation to a determination of whether the parameters monitored by the processor exceed a condition associated with a loss of contact of the burr tool 16. For instance, the rules may relate to one or more of the acceleration threshold value and/or force threshold value described above. For instance, the processor of the detection module may apply a rule wherein if a monitored parameter exceeds the threshold value established for that parameter, a loss of contact is detected, and the detection module may cease operation of the instrument and/or apply a brake. In some embodiments, a rule may be established that requires simultaneous occurrence of exceeding the threshold value for acceleration and force for detection of a loss of contact of the burr tool 16. In other embodiments, structures other than a processor and memory may be provided to execute the detection module such as application specific integrated circuits (ASICs), field programmable gate arrays, or other appropriate hardware and/or software. Further still, the detection module may be integrated into an instrument controller or provided as an independent module for execution in connection with the instrument.

As a further safety feature of the instrument (e.g., that may be especially helpful for operations involving a burr tool 16), upon initiation of rotation of the instrument 16, the acceleration of the rotational speed of the instrument may be ramped such that top rotational speed of the instrument is reached relatively gradually. This value may be preset or adjustable by the user. In this regard, upon initiation of rotation, the instrument may begin to rotate relatively slowly with gradual (e.g., a set or variable increase over time) ramping up of the speed of the instrument. This may be a linear increase, an exponential increase, or stepped increase in speed without limitation.

While the invention has been illustrated and described in detail in the drawings and foregoing description, such illustration and description are to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for use of an instrument, comprising:
operating an instrument to perform an operation relative to a bone of a patient by contacting a working portion of the instrument with the bone of the patient;
monitoring the working portion of the instrument;
detecting a loss of contact between the working portion and the bone; and
arresting the instrument upon detection of the loss of contact between the working portion and the bone.

2. The method of claim 1, wherein the monitoring comprises measuring one or more parameter using a measurement system of the instrument.

3. The method of claim 2, wherein the measurement system comprises an acceleration sensor and the one or more parameters is an acceleration of the working tool relative to the bone.

4. The method of claim 3, wherein the detecting comprises measuring the acceleration of the working tool relative to a bone that exceeds an acceleration threshold value.

5. The method of claim 2, wherein the measurement system comprises a force sensor and the one or more parameters is a change in force acting on the working tool.

6. The method of claim 5, wherein the detecting comprises measuring the change in force acting on the working tool that exceeds a force threshold value comprising a maximum rate of change in force.

7. The method of claim 1, wherein the arresting comprises ceasing operation of a drive system of the instrument.

8. The method of claim 7, wherein the arresting comprises applying a brake to a drive system of the instrument.

* * * * *